(12) United States Patent
Weiss et al.

(10) Patent No.: US 8,321,034 B2
(45) Date of Patent: Nov. 27, 2012

(54) STIMULATION ELECTRODE LEAD

(75) Inventors: Ingo Weiss, Berlin (DE); Stefan Knorr, Berlin (DE); Michelle Maxfield, Berlin (DE); Michael Friedrich, Kleinmachnow (DE)

(73) Assignee: BIOTRONIK CRM Patent AG (CH)

( * ) Notice: Subject to any disclaimer, the term of this patent is extended or adjusted under 35 U.S.C. 154(b) by 266 days.

(21) Appl. No.: 12/723,715

(22) Filed: Mar. 15, 2010

(65) Prior Publication Data

US 2010/0256721 A1 Oct. 7, 2010

(30) Foreign Application Priority Data

Apr. 2, 2009 (DE) .......... 10 2009 002 152

(51) Int. Cl.
*A61N 1/04* (2006.01)

(52) U.S. Cl. .................................................. 607/116

(58) Field of Classification Search ........... 607/116–118
See application file for complete search history.

(56) References Cited

U.S. PATENT DOCUMENTS

| 5,257,635 A | 11/1993 | Langberg |
| 5,545,201 A | 8/1996 | Helland et al. |
| 5,571,157 A | 11/1996 | McConnell |
| 6,687,550 B1 | 2/2004 | Doan |
| 2007/0299493 A1 | 12/2007 | Osypka |
| 2008/0071313 A1 | 3/2008 | Stevenson |
| 2008/0269591 A1 | 10/2008 | Halperin et al. |
| 2010/0016936 A1 | 1/2010 | Stevenson et al. |

FOREIGN PATENT DOCUMENTS

WO　WO 02/083016 A1　10/2002

OTHER PUBLICATIONS

European Search Report, EP 10 15 5869, Jan. 11, 2011.

*Primary Examiner* — Scott Getzow
*Assistant Examiner* — Amanda Patton
(74) *Attorney, Agent, or Firm* — Craig A. Fieschko, Esq.; DeWitt Ross & Stevens S.C.

(57) ABSTRACT

An implantable stimulation electrode lead for medical purposes includes a coaxial lead structure with an inner supply lead and an outer supply lead electrically insulated from the inner supply lead, and first and second electrodes which are provided at or near the distal end of the lead structure. The outer supply lead is guided to the first electrode, which is at the tip of the lead structure, and the inner supply lead is guided to the second electrode, which is proximal to the first electrode, such that the electrical connections cross over along the radius of the device.

23 Claims, 12 Drawing Sheets

FIG. 11

STIMULATION ELECTRODE LEAD

FIELD OF THE INVENTION

The invention relates to an implantable stimulation electrode lead used medically to electrically stimulate biological tissue and/or organs, and an implantable stimulation arrangement.

BACKGROUND OF THE INVENTION

Elongated electrode leads, in particular stimulation electrode leads, are an important component of many electric systems that are used in medicine for diagnostic and/or therapeutic purposes, such as (for example) pacemakers, defibrillators, neurostimulators, and catheter systems.

Figure 1:
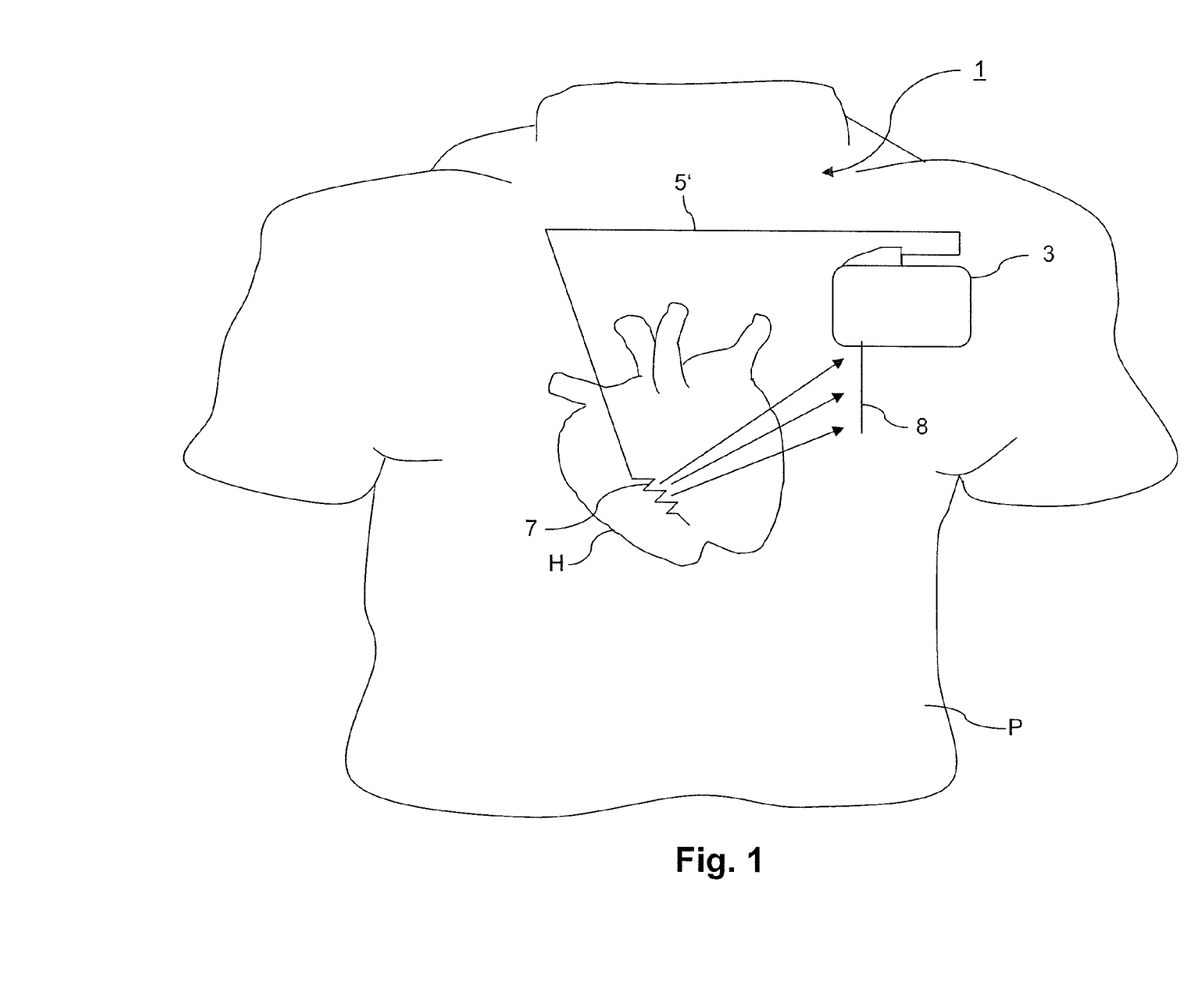
FIG. 1: A schematic representation of an implantable defibrillation arrangement.

FIG. 1 shows the basic structure of an implantable defibrillation arrangement 1, as is known from U.S. Pat. No. 5,531, 766. In order to stimulate the heart H of a patient P, a defibrillator 3 is electrically connected to an electrode lead 5', which here bears a special electrode ("shock electrode") 7, which is located at the distal end thereof and is implanted in the patient's heart. Defibrillation is performed via a current path between this electrode and a counter electrode that is located at a distance from the heart. The housing 8 of the defibrillator 3, which contains the units for detecting heart signals and generating electric impulses, can act as a counter electrode. Alternatively, a counter electrode can be attached to the electrode lead or on the outside of the housing.

Stimulation electrode leads usually have a supply lead structure with a distal end including conductive contacts or electrodes, which produce an electrical connection to the surrounding tissue and/or organ of a patient and which are provided for measurement and/or stimulation purposes. If a stimulation electrode lead has several of such electrodes, the supply lead structure may also include several conductors insulated from one another, which are often arranged in a coaxial manner.

Figure 2A:
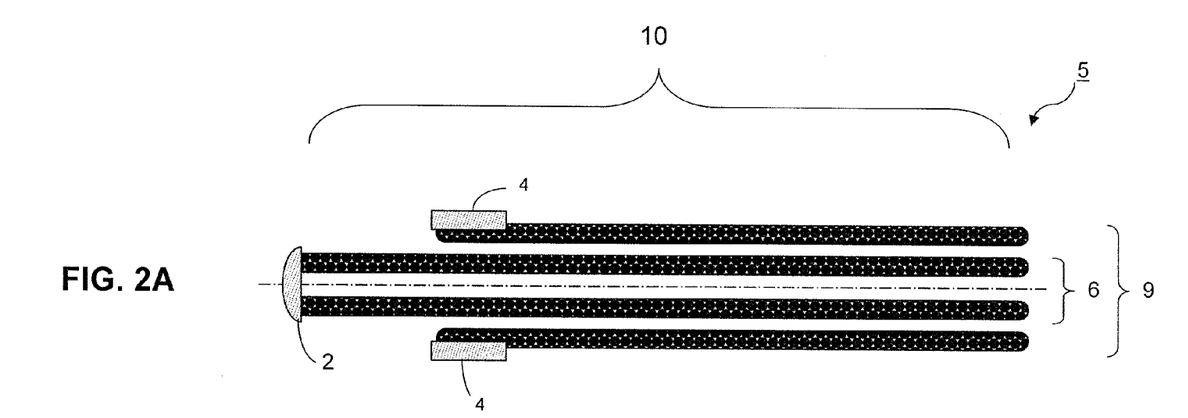
FIG. 2a-2c: Schematic representations of a stimulation electrode lead according to the prior art.
Figure 2B:
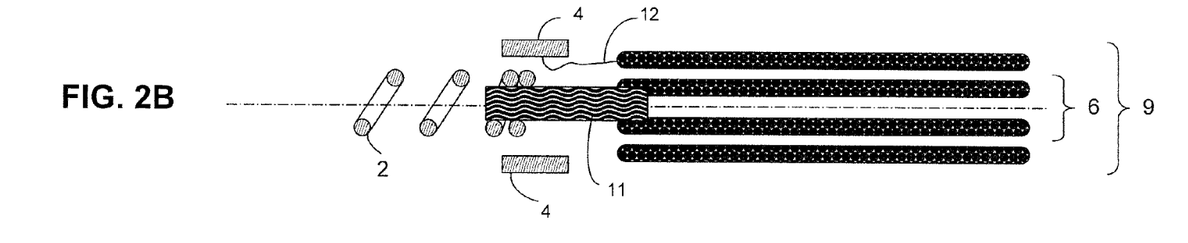
Figure 2C:
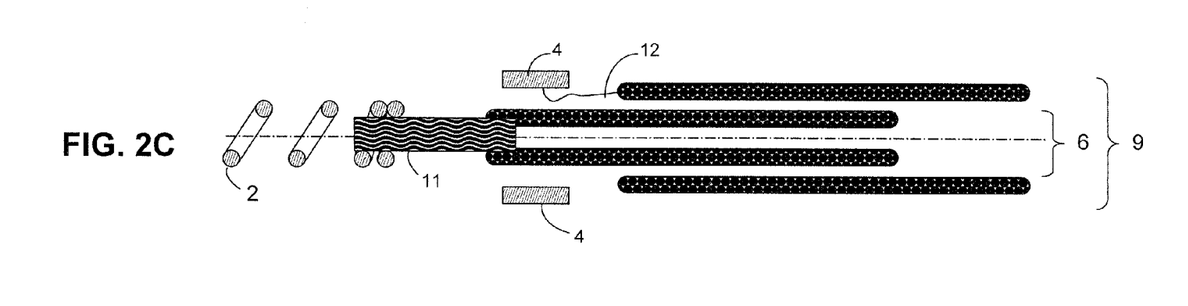

FIGS. 2a-2c show a schematic representation of a standard stimulation electrode lead 5, in which two electrodes 2, 4 are present on the distal end of the supply lead structure 10, wherein one electrode (tip electrode) 2 forms a contact at the end of the lead structure 10 and the other electrode (annular electrode) 4 forms an annular contact around the lead structure 10. Since two electrodes are present, the supply lead structure 10 includes two leads 6, 9, which are arranged coaxially.

The stimulation electrode leads can be passively fixable electrode leads (FIG. 2a), wherein the inner supply lead 6 is fixed relative to the outer supply lead 9, or actively fixable electrode leads (FIG. 2b-c), wherein the inner supply lead 6 is moveable relative to the outer supply lead 9. In the latter case, the inner supply lead 6 may be rotationally displaced relative to the outer supply lead 9 in order to introduce or screw the tip electrode 2 into the tissue. In particular, a tip electrode 2 may have the shape of a screw helix.

In both configurations, the outer supply lead 9 of the supply lead structure 10 leads to the annular electrode 4 and the inner supply lead 6 leads to the tip electrode 2. The contact between the supply leads and the electrodes is carried out either directly (FIG. 2a) or by a conductive connection element (FIG. 2b-c), e.g., a mounting fitting 11 or an electric cable 12.

Although this construction is relatively simple from a mechanical viewpoint and is easy to implement structurally, it can have negative effects from an electrical viewpoint. Stimulation electrode leads of this type can lead to certain problems when they are exposed to electromagnetic fields generated by modern examination and diagnostic equipment.

SUMMARY OF PREFERRED VERSIONS OF THE INVENTION

An object of the invention is to provide an improved stimulation electrode lead or stimulation arrangement which substantially reduces or eliminates the foregoing problems. An implantable stimulation electrode lead of this nature may include a coaxial lead structure with an inner supply lead and an outer supply lead, wherein the two supply leads are electrically insulated from one another. A first and a second electrode are provided at or near to the distal end of the lead structure, wherein the first electrode is at the tip of the lead structure and the second electrode is situated proximally with respect to the first electrode. The stimulation electrode lead has electrical connections between the supply leads and the electrodes which are "crossed over" such that the inner supply lead is guided to the second electrode and the outer supply lead is guided to the first electrode.

This solution can be used for a passively fixable stimulation electrode lead wherein the inner supply lead is fixed relative to the outer supply lead, as well as for an actively fixable stimulation electrode lead wherein the inner supply lead is moveable relative to the outer supply lead. In the latter case, the inner supply lead can be displaceable or rotatable with respect to the outer supply lead, wherein the first electrode can be, for example, a tip with a barb or a screw, which is inserted or screwed into the tissue with the inner supply lead. In particular, the first electrode can form a contact at the tip of the lead structure and the second electrode can form an annular contact around the lead structure. Moreover, the electrode lead can be monopolar or bipolar.

Different configurations are possible in the case of the actively fixable stimulation electrode. In a first configuration, the inner supply lead is moved by rotation and its end is displaced with respect to the end of the outer supply lead. Since both of the supply leads at the proximal end are in a fixed positional relationship to one another, the outer supply lead can be compressed and/or the inner supply lead must be stretched. The rotation and the displacement of the inner supply lead are transferred via a transfer element to the first electrode. The transfer element, which has a low longitudinal stiffness, connects the inner supply lead to the first electrode without producing a conducive contact, and thus only mechanical loads (forces and moments) of the inner supply lead are transferred.

In a second configuration, the inner supply lead is only rotated and is not displaced with respect to the outer supply lead. Consequently, the supply leads are not stretched or compressed by the rotation, and the force needed for unscrewing the first electrode is reduced and the mechanical stress of the supply leads is reduced. The moment for unscrewing the first electrode is likewise transferred from the inner supply lead via a transfer element. This element can change its length in order to displace the first electrode relative to the second electrode.

In order to insert the first electrode into the tissue and to fix it there, a means for active fixing can act with the transfer element. This means can be a spring, for example, which acts on the transfer element by a pressure or a moment in order to hold the first electrode in a specific position.

The connection between the electrodes and the supply leads can be carried out by electrical connecting leads such as wires or cables. However, a twisting of the inner supply lead with respect to the outer supply lead also results in a twisting and stretching of the connecting wires. Flexible electric wires can therefore be used as connecting leads. Preferably, these flexible wires can be composed of stretchable material in order to avoid an undesirable interlacing of the wires while screwing in or unscrewing the inner supply lead.

In one version of the invention, the electrical connecting leads crossing over one another are provided as a helix structure. This helix structure can be situated along or around the transfer element arranged between the inner supply lead and the first electrode or around it. When the inner supply line or the tip electrode is unscrewed, the helix structure is extended in the longitudinal direction and the number of coils is reduced. The mechanical stress on the electrical connection leads during rotation is thus greatly reduced. In a preferred design, the electrical connection from the inner supply line is fed through forwards along the transfer element and subsequently guided back as a helix to the second electrode. The electrical connection of the outer supply line, in contrast, is guided directly as a helix to the first electrode.

Flexible wires, stranded wires, cables or the like are preferably used as material for the electrical connections. At least one of the connecting leads should be insulated in order to avoid a short circuit. Most preferably, both flexible connecting leads are insulated from one another. In order not to reduce the diameter of the helix structure when unscrewing, the winding of the electrical wires preferably has a counter direction of rotation to the unscrewing direction.

As an alternative to an insulating transfer element between the inner supply lead and the first electrode, a conductive structure can be used, which is insulated only on the distal end. An electrical lead that connects the inner supply lead to the distal end of the helix structure can thus be omitted.

However, the connecting leads can be guided around the inner supply lead as a helix structure. In contrast to the previously described arrangements, in a construction of this type the mechanical properties of the stimulation electrode lead are influenced only slightly and provide only minor stiffening in the distal region of the stimulation electrode lead.

When the geometric parameters of the helix structure are correctly dimensioned, the diameter of the helix does not change when the tip electrode is unscrewed, so that very little space for the helix is needed in the electrode lead. An isodiametric helix structure of this type has the advantage that the entire helix deformation can take place in a cylindrical/annular space crossover of adjacent electrical connecting leads is presented where the thickness of the cylindrical/annular space is only slightly greater than the wire diameter.

Expediently, the helix can also be formed of coaxial connecting leads, multi-member stranded wires, wires with an angular cross section or other lead structures.

In another version, the transfer element has the shape of a hollow spiral. The wires which connect the inner supply lead to the second electrode, and the outer supply lead to the first electrode, can run in the interior of the spiral. The spiral can be composed entirely of insulating material, or it can be conductive apart from the front part that is in contact with the first electrode. When the inner supply lead is unscrewed, the wires twist inside the spiral. If the first electrode has the shape of a screw, the pitch of the spiral can preferably be the same as the screw pitch. The location at which the wires extend into the spiral is thus independent of the position of the screw.

In an alternative version of the invention, a spiral spring can be used instead of flexible connecting leads for the electrical connection of the inner supply lead to the second electrode and the outer supply lead to the first electrode. The spiral spring can have an outer and an inner section, wherein the outer section is stationary and the inner section can rotate with respect to the outer section. The spring is deformed when the inner supply lead or the first electrode is unscrewed. The spiral spring can be composed of metal, insulated metal, metallized plastic or other conductive structures.

When more than one lead is necessary, a separate spiral spring can be used for each lead or alternatively a single spring with several leads can be used.

The spiral spring can be formed of a wound substrate which is metallized on both sides, wherein the metallization on one side of the substrate produces the connection of the inner supply lead to the second electrode, and the metallization on the other side of the substrate produces the connection of the outer supply lead to the first electrode. In one possible design, one of the metallization layers is completely insulated.

In a further version of the invention, the spring force of the spiral spring acts against each rotation of the inner supply lead or of the first electrode. For this reason the spring rigidity should be low in order to allow a rotation without great resistance. A low rigidity can be achieved through a high number of coils and a low bending stiffness. The rest position of the spring represents the unscrewed position, thereby preventing the restoring force of the spring from accidentally screwing back the first electrode again. This results in a stimulation electrode lead with a retracted first electrode, so that the spring is preloaded. When the inner supply lead or the first electrode is unscrewed, the spring relaxes, whereby the unscrewing movement is supported. In this configuration the spring leads to the active fixing of the first electrode.

Instead of a complete metallization of the substrate, one of the two leads at the end of the substrate can be plated through. This has the advantage that contacting of the metallized areas is possible from only one side, the inner side or the outer side.

As another version, the ends of the substrate can be bent such that a spiral spring with a variable diameter is produced, so that parts of the electrode lead with different diameters can be connected to one another.

In another version of the invention, a conductive adapter can be present between the spiral spring and the first or the second electrode, and/or the inner supply lead or the outer supply lead, which has other mechanical properties from those of the substrate of the spiral spring. Direct contact between the substrate and the components of the electrode lead can thus be avoided in order to achieve improved mechanical stability. This adapter can be a ceramic tube that has on its surface several metallizations that ensure the electrical connection between the metallization layers of the spring and the electrodes or the supply leads. The contact of the second electrode can be replaced by the outer metallization of the adapter.

In another version of the invention, a tubular structure with an integrated lead crossover can be used instead of flexible connecting leads or the spiral spring for the electrical connection of the inner supply lead to the second electrode, and of the outer supply lead to the first electrode. This structure can use a ceramic tube, the inside and outside of which is metallized such that several through-contacts extend radially through the tube lead to the desired crossover. The outer shape of the structure and the contact areas can be cylindrical.

In order to increase the flexibility of the inner supply lead relative to the outer supply lead, the tubular structure can be coupled with a distal conductive helix to connect the outer supply lead to the first electrode and to a proximal conductive spiral, parallel to the distal spiral, to connect the inner supply lead to the second electrode. In contrast to the spiral spring referenced above, these distal and proximal helices are not composed of a wound metallized substrate. The substrate is therefore not necessary, and the spiral can be composed, if necessary, of an insulated metal strip that is wound to form a helix. As an advantage, this spiral requires less overall height, and the lower stiffness of these spirals produces a lower undesirable return torque.

In the foregoing version with two spirals arranged in a parallel manner, there can be difficulty maintaining the lead crossover. In order to circumvent the crossover, preferably the connecting lead can be guided from the outer supply line to the first electrode outside via the second electrode. In an alternative manner, the second electrode, which forms an annular contact, can have a bore through which the lead is guided; or the annular contact can be replaced by a cylinder ring segment, through the gap of which a lead is guided; or the annular contact can include an insulator, which is partially metallized and has a conductive bushing.

To transmit the electrical signals between two supply leads rotated relative to one another, sliding contacts can also be used instead of the spiral springs or helices. A construction similar to that of a ball bearing is also conceivable, wherein the balls, the surfaces of which are conductive, are used to transmit the electrical signals. Alternatively, conductive liquid can also be used, which is located in the thin gap between two conductive contacts and electrically connects them to one another. If the gap is thin enough, substances can also be used with a relatively high resistance. The use of liquid metals with a correspondingly high conductivity is also conceivable. The principle of the ball bearing can be combined as desired with that of the conductive liquid.

In the foregoing versions, all of the components that move past one another during the unscrewing operation preferably have the most low-friction surface possible in order to generate little mechanical resistance. This can be achieved by suitable coatings, such as, e.g., Teflon or SilGlide. Moreover, the helix structures of the connecting leads can optionally be coated with a hose or cast in order to produce a smooth surface, whereby it is almost impossible for the leads of the helix to snag during the unscrewing operation.

In another version of the invention, the electrical crossover can also take place several times in one of the electrodes. Another crossover can also be useful in order to achieve the same plug configuration (e.g., IS-1) as previous systems. To this end, a further crossover can be directly integrated into the IS-1 plug.

The concept of the crossed leads in principle can also be applied to electrode leads with more than two supply leads.

An exemplary stimulation arrangement connects one of the stimulation electrode leads described above at the proximal end to an implantable device, e.g., a defibrillator, a pacemaker or a neurostimulator. The device has a housing, which generally contains a control unit for sensing or generating electrical pulses, and a battery for power supply. In addition to electrodes for electrical stimulation, the stimulation electrode lead can have a sensor or a sensing electrode, e.g., for sensing tissue action potentials and/or organ action potentials.

With respect to prior implantable stimulation arrangements, it is advantageous that with arrangements according to the invention, the fault problems due to the use of modern examination devices that generate electromagnetic fields are eliminated or at least reduced.

BRIEF DESCRIPTION OF THE DRAWINGS

Advantages and expedient features of the invention are reviewed in the following description of selected exemplary versions of the invention shown in the Figures, which include.

DETAILED DESCRIPTION OF EXEMPLARY VERSIONS OF THE INVENTION

Figure 3A:
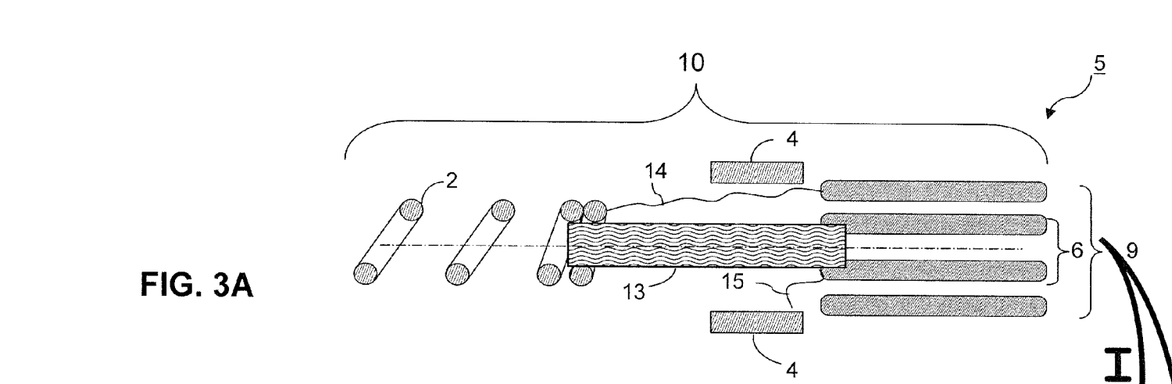
FIG. 3a-3c: Schematic representations of an exemplary stimulation electrode lead according to the invention.

FIG. 3a shows the distal end of an implantable stimulation electrode lead 5, in particular an actively fixable stimulation electrode lead 5, with a lead structure 10 including an inner supply lead 6 and an outer supply lead 9. A first and a second electrode 2, 4 are present at the distal end of the lead structure 10, wherein the first electrode 2 has the shape of a screw helix (screw electrode) and the second electrode 4 has the shape of a ring (annular electrode) around the lead structure 10. The first electrode 2 is connected to a transfer element 13 composed of insulated material. Flexible and stretchable electrical leads 14, 15 provide the electrical connection between the outer supply lead 9 and the screw electrode 2 or the inner supply lead 6 and the annular electrode 4.

Figure 3B:
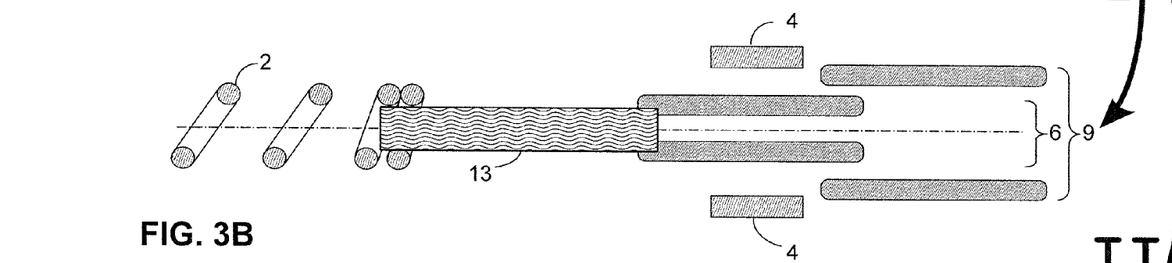

FIG. 3b shows a first configuration (I) of the stimulation electrode lead 5 in an extended state, wherein the inner supply lead 6 is displaced relative to the outer supply lead 9 by screwing. The result of the twisting of the inner supply lead 6 with respect to the outer supply lead 9 is that the connecting electrical leads 14, 15 (not shown in the figure) twist and are extended.

Figure 3C:
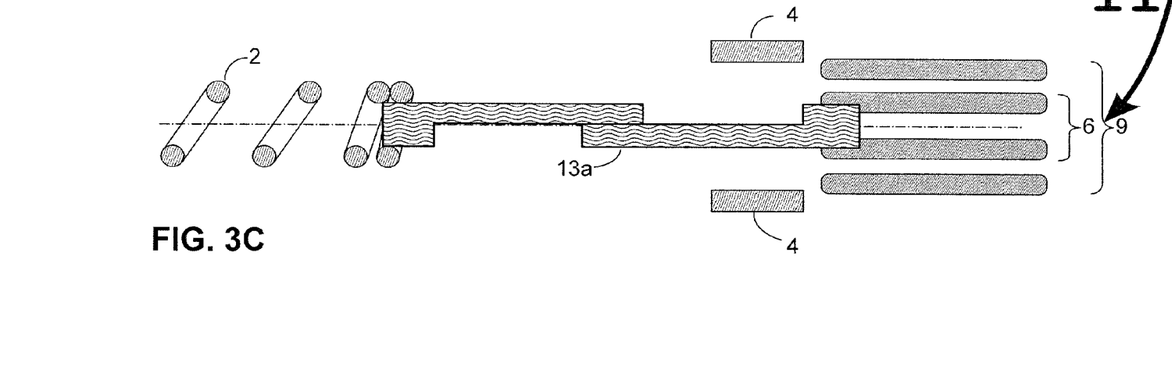

FIG. 3c shows a second configuration (II) of the stimulation electrode lead 5 in the extended state, wherein the inner supply lead 6 is only rotated with respect to the outer supply lead 9 and is not displaced. The screw 2 is displaced relative to the annular electrode 4 by an extendible transfer element 13a, which changes its length during the unscrewing of the inner supply lead 6. The twisting of the inner supply lead 6 with respect to the outer supply lead 9 likewise results in a twisting and extension of the electrical leads 14, 15 (not shown in the figure).

Figure 4A:
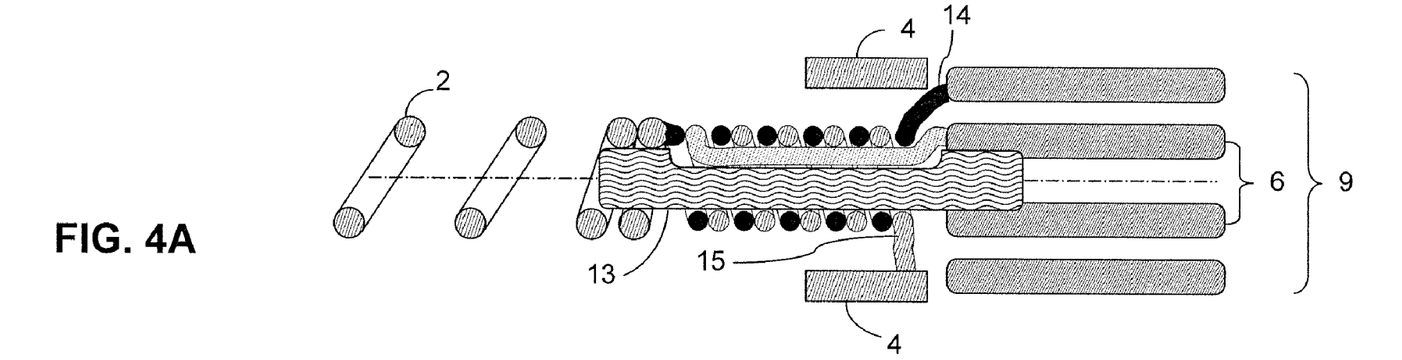
FIGS. 4a and 4b: Schematic representations of another exemplary stimulation electrode lead with a helix structure for the electrical connection.

FIG. 4a shows the distal end of a stimulation electrode lead 5 as in FIG. 3a, in which both of the electrical connecting leads 14, 15 are provided as a helix around the transfer element 13. The electrical connection 15 is led through from the inner supply lead 6 to the front along the transfer element 13, and subsequently guided back as a helix up to the annular electrode. The electrical connection 14 of the outer supply lead 9 is guided as a helix directly to the screw electrode.

Figure 4B:
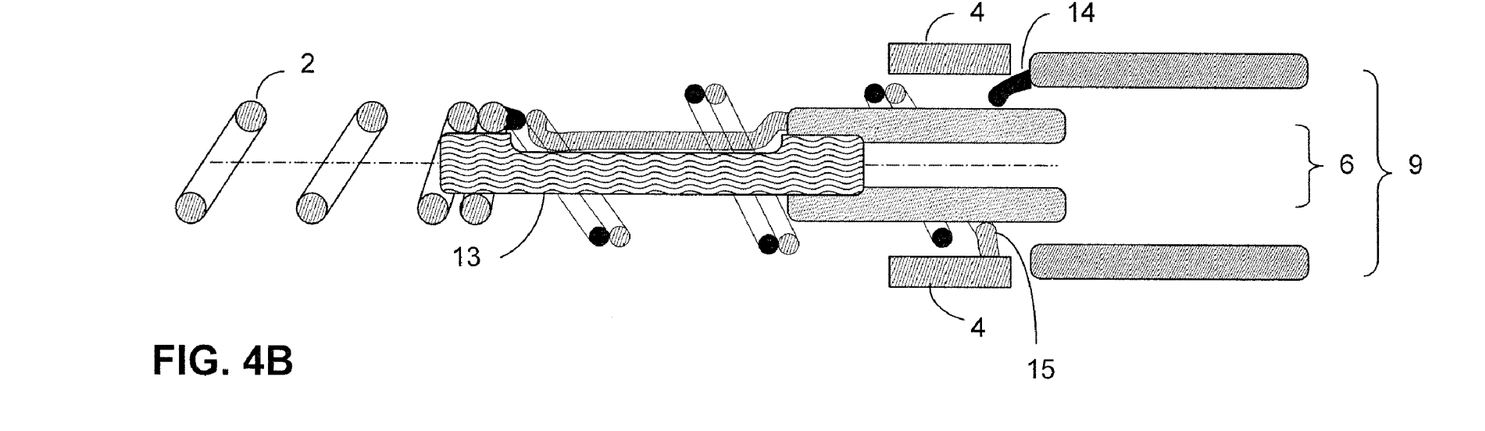

FIG. 4b shows the unscrewed state of the stimulation electrode lead 5 of FIG. 4a. During the unscrewing of the screw 2, the helix is extended and the number of coils is reduced.

Figure 5A:
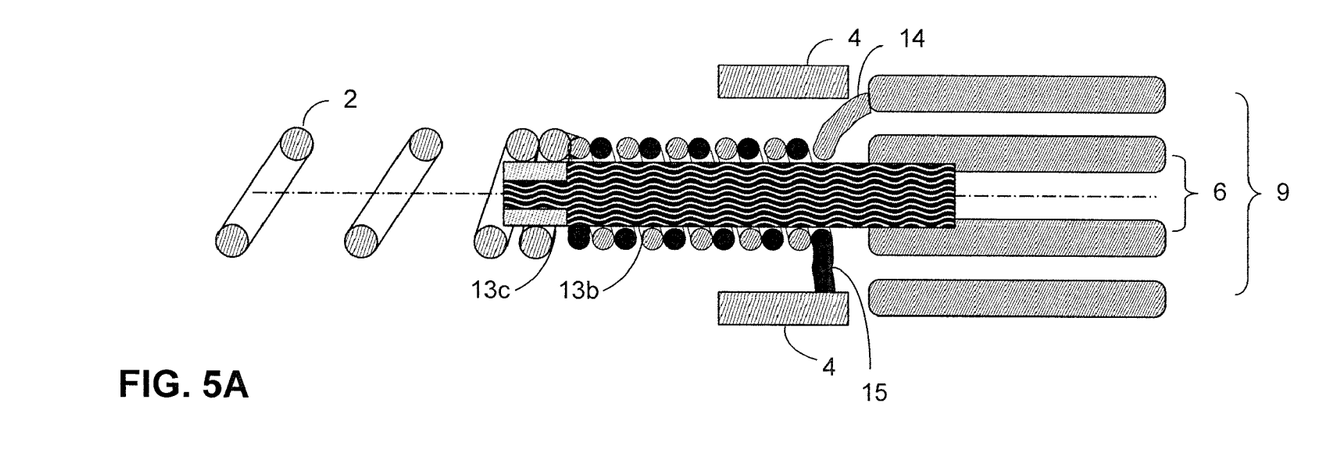
FIGS. 5a and 5b: Schematic representations of another exemplary stimulation electrode lead with a helix structure for the electrical connection.

FIG. 5a shows a variant of the electrode lead from FIG. 4a, in which the transfer element 13b is composed of a conductive material. An insulating structure 13c is present on the distal end of the transfer element 13b in order to prevent a conductive connection between the inner supply lead 6 and the screw electrode 2. As can be seen from the figure, the feedthrough of the electrical connection 15 from the inner supply lead 6 to the front along the transfer element 13b is no longer necessary.

Figure 5B:
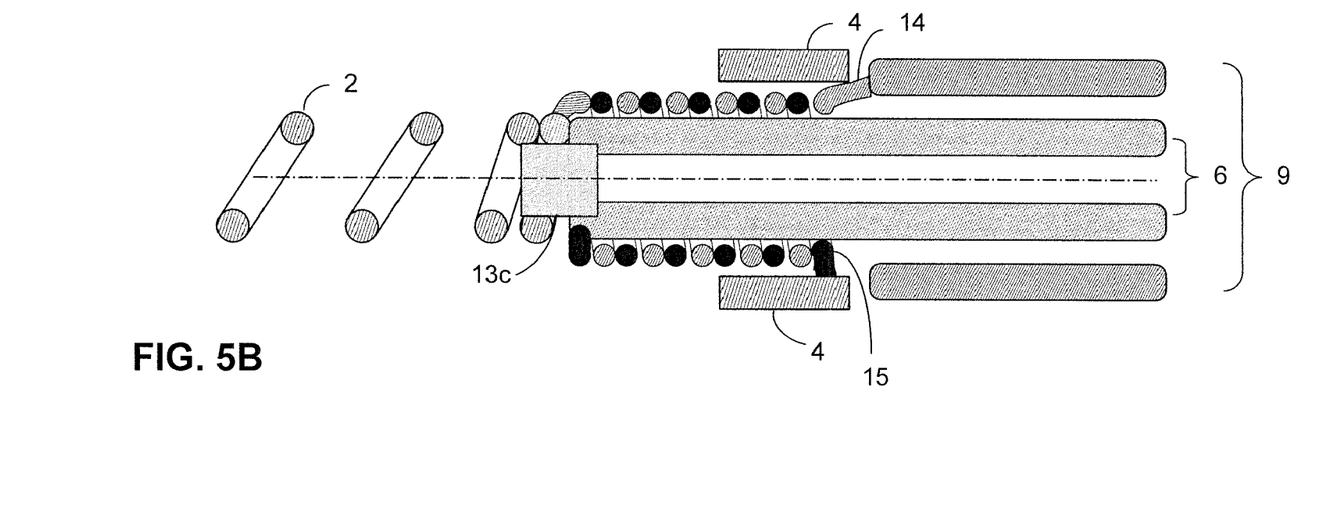

FIG. 5b shows a further variant of the electrode lead from FIG. 4A, in which the helix structure is situated around the inner supply lead 6. In order to prevent a conductive connection between the inner supply lead 6 and the screw electrode 2, an insulating structure 13c is again present to hold the screw electrode 2.

Figure 6A:
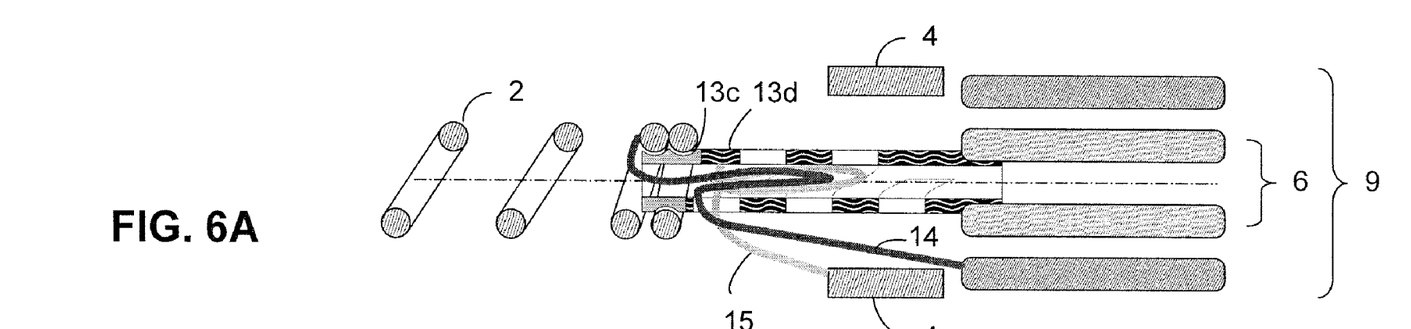
FIGS. 6a and 6b: Schematic representations of another exemplary stimulation electrode lead with a hollow spiral as a transfer.
Figure 6B:
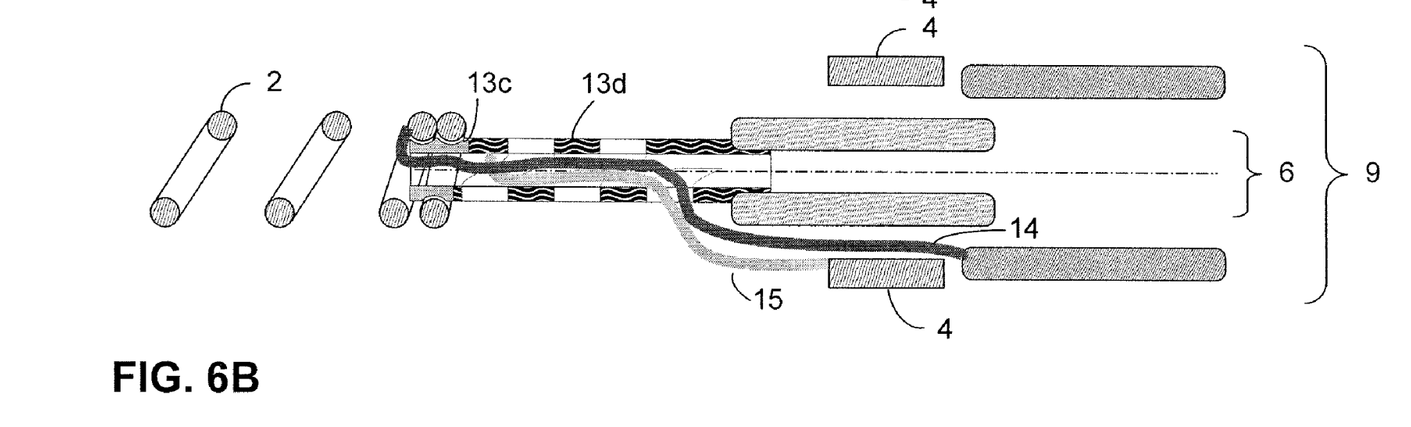

FIGS. 6a and 6b show the distal end of a stimulation electrode lead 5 similar to FIG. 3a, in which the transfer element has the shape of a hollow helix 13d in which the connecting leads 14, 15 run. In particular, the leads 14, 15 in the non-unscrewed state (FIG. 6a) extend into the distal region of the hollow helix 13d, while the wires 14, 15 in the unscrewed state (FIG. 6b) extend into the proximal region of the hollow spiral 13d. The pitch of the screw electrode 2 is identical to the pitch of the hollow helix 13d in order to reduce the mechanical stress on the connecting leads 14, 15 during rotation. The hollow helix 13d is composed of conductive material, wherein the front section, which is in contact with the first electrode 2, is electrically insulated.

Figures 7A, 7B:
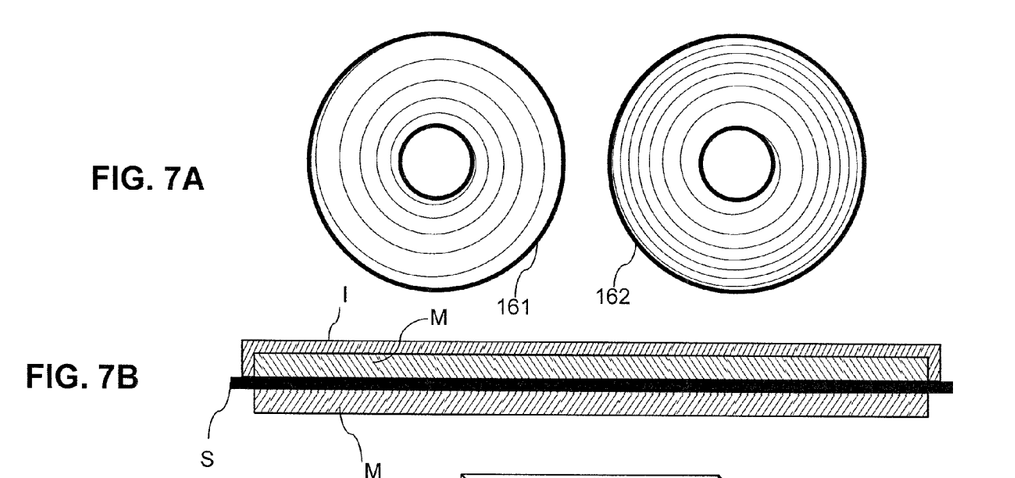
FIG. 7a-7c: A schematic representation of a spiral spring for the electrical connection.
Figure 7C:
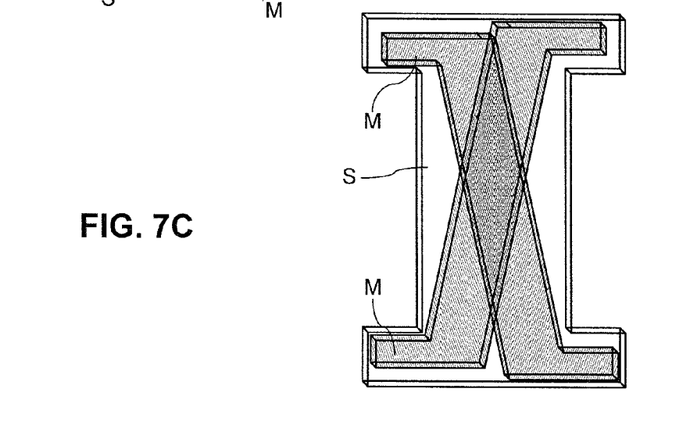

FIGS. 7a through 7c show a possible version of a spiral spring 16 for the electrical connection for a stimulation electrode lead 5. The spiral spring includes an inner part 161 and an outer part 162, which produce the contacts between the parts counter-rotated with respect to one another of the electrode lead 5. The spiral spring is composed of four layers: a substrate S, two metal layers M which are located on the opposing sides of the substrate S, and an insulating layer I, which completely covers one of the metallization layers.

As shown in FIG. 7c, a plastic film S with an H-shape is metallized on each side, wherein each metallization layer M runs diagonally. The spiral spring 16 is thereby produced during the winding of the plastic film S, wherein the center bar of the H serves as the actual spring 16, while the ends serve to contact the metallizations M.

Figure 8A:
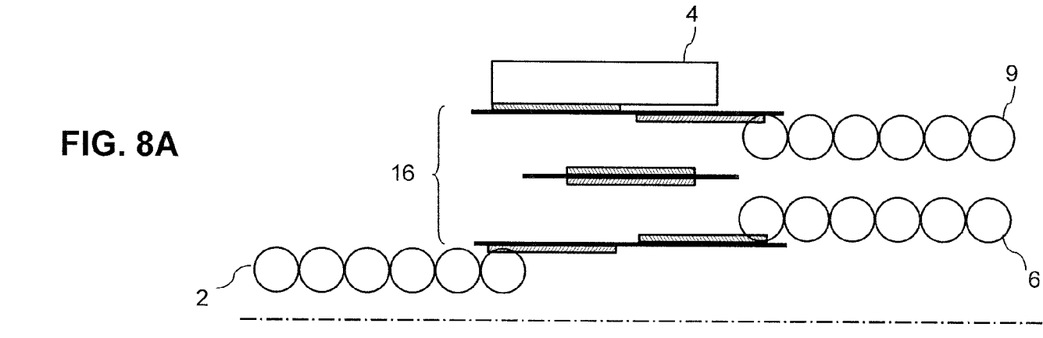
FIG. 8a-8d: Schematic representations of a stimulation electrode lead with a spiral spring for the electrical.

FIG. 8a shows the upper cross section of the distal end of the stimulation electrode lead 5, in which the spiral spring 16 shown as in FIG. 7 is used for the electrical connection between the inner supply lead 6 and the second electrode 4 or between the outer supply lead 9 and the first electrode 2. The H-structure of FIG. 7c is shown in rolled up form (wound twice) and in cross section at different points. The outer metallization of the spiral spring 16 connects the second electrode 4 to the inner supply lead 6, while the inner metallization contacts the first electrode 2 to the outer supply lead 9.

Figure 8B:
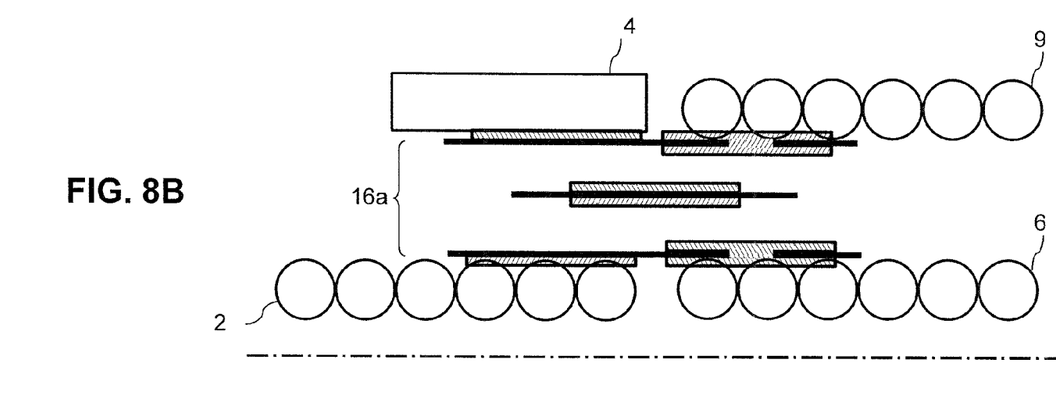
Figure 8C:
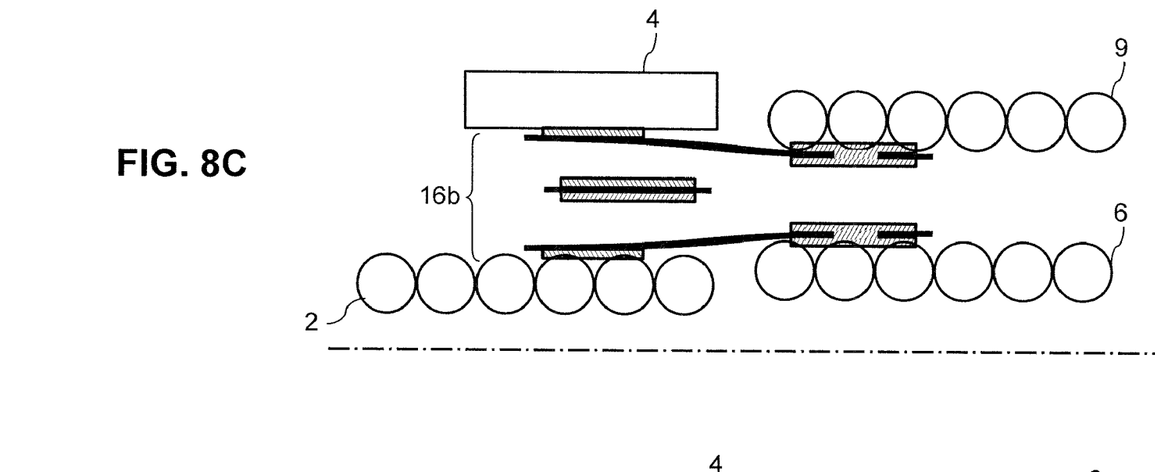

FIG. 8b shows a variant of the structure of the spiral spring of FIGS. 7a-7c, wherein two through-contacts are used to contact the spiral spring 16a only from their outside. FIG. 8c shows another variant, wherein the ends of the substrate S are bent in order to achieve a spiral spring 16b with a variable diameter.

Figure 8D:
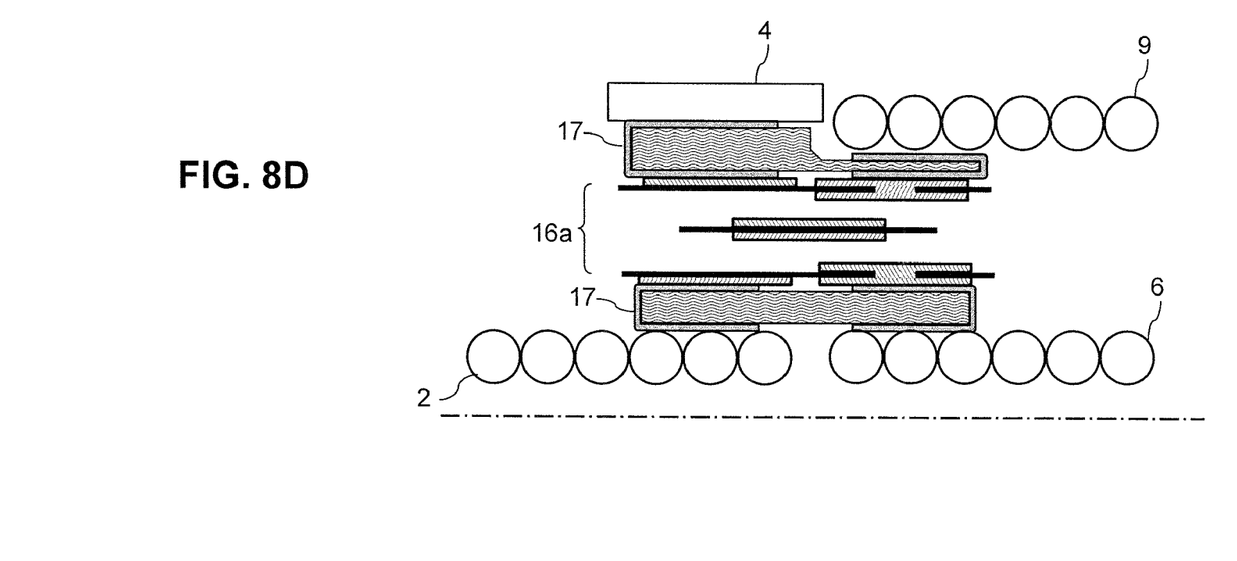

FIG. 8d shows another version in which a ceramic tube 17 is arranged between the spiral spring 16a, which has only contacts from outside, and the components of the electrode lead 5. The ceramic tube 17 has several metallizations in order to ensure the electrical connection between the inner supply lead 6 and the second electrode 4, and/or between the outer supply lead 9 and the first electrode 2, through the spiral spring 16a.

Figure 9:
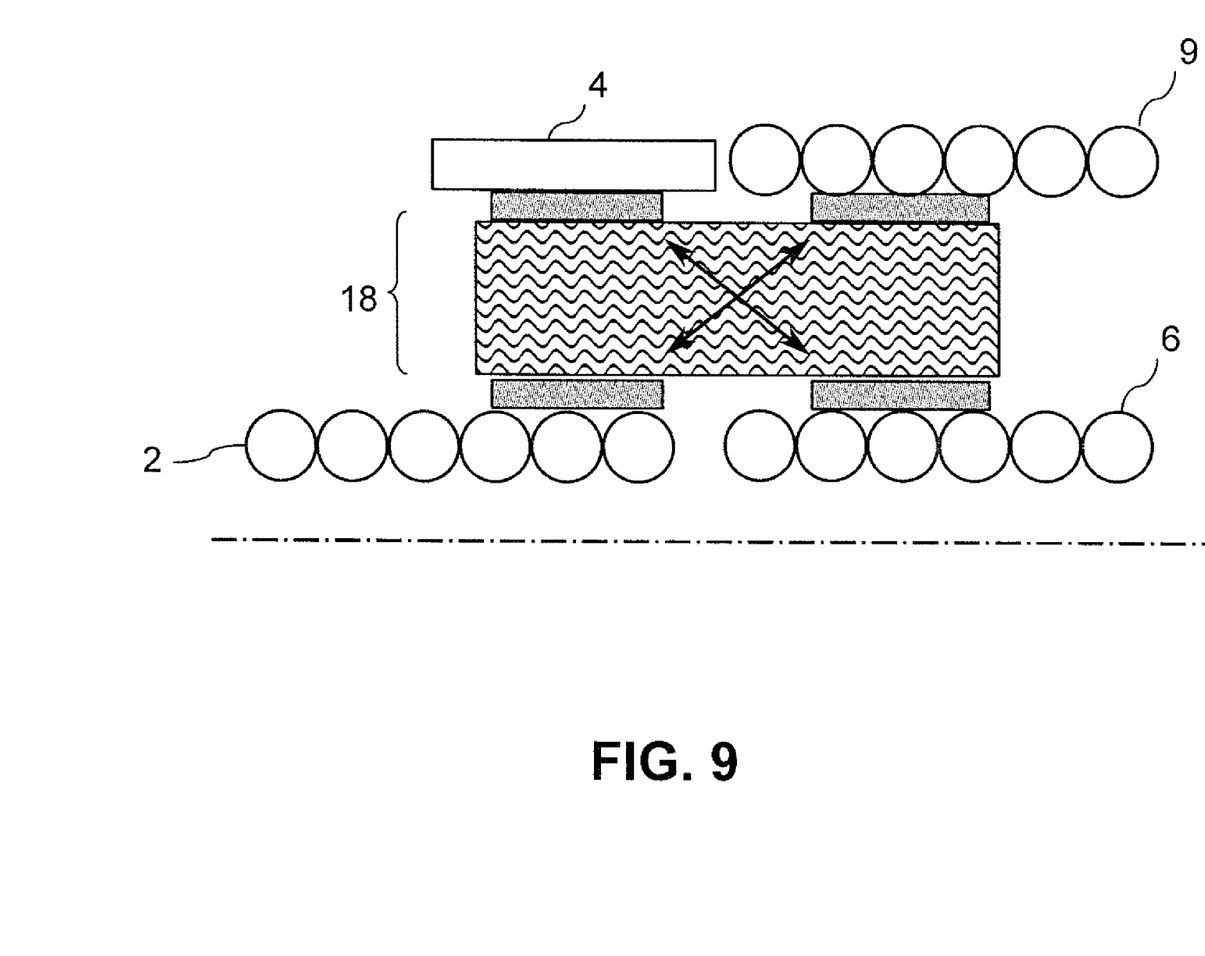
FIG. 9: A schematic representation of a stimulation electrode lead with a tubular structure with integrated lead crossover for the electrical connection.

FIG. 9 shows the upper cross section of the distal end of the stimulation electrode lead 5, in which a ceramic tube 18 has an integrated lead crossover for electrical connection between the inner supply lead 6 and the second electrode 4 or between the outer supply lead 9 and the first electrode 2.

Figure 10A:
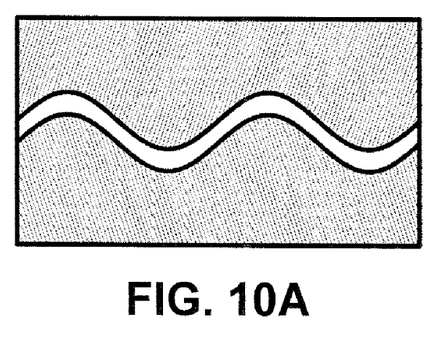
FIG. 10a-10d: Schematic representations of unwound metallization surfaces of a tubular structure with integrated lead crossover.
Figure 10B:
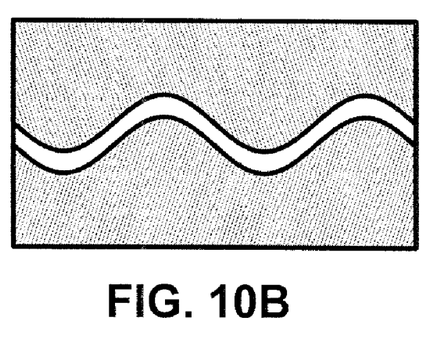
Figure 10C:
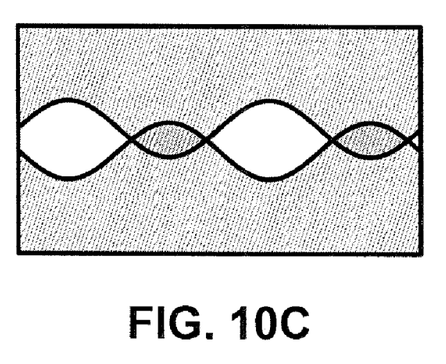
Figure 10D:
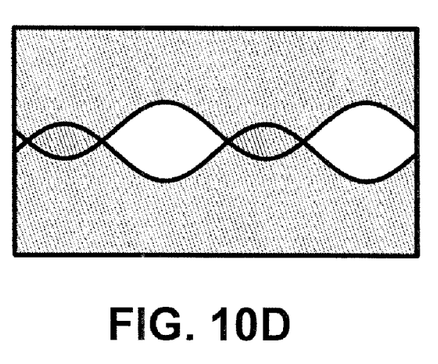

The metallization surfaces of the ceramic tube 18 are shown in unwound form in FIGS. 10a through 10d, wherein FIGS. 10a and 10c represent the metallization of the outer surface and FIGS. 10b and 10d represent the metallization of the inner surface. To illustrate the contact of both sides, the inner and outer surfaces are shown together, wherein in each case only one electric pole of the component is shown. At the points at which the inner and outer surface of the metallization of a pole overlap, through-contacts are produced to connect the inner and outer surface.

Figure 11:
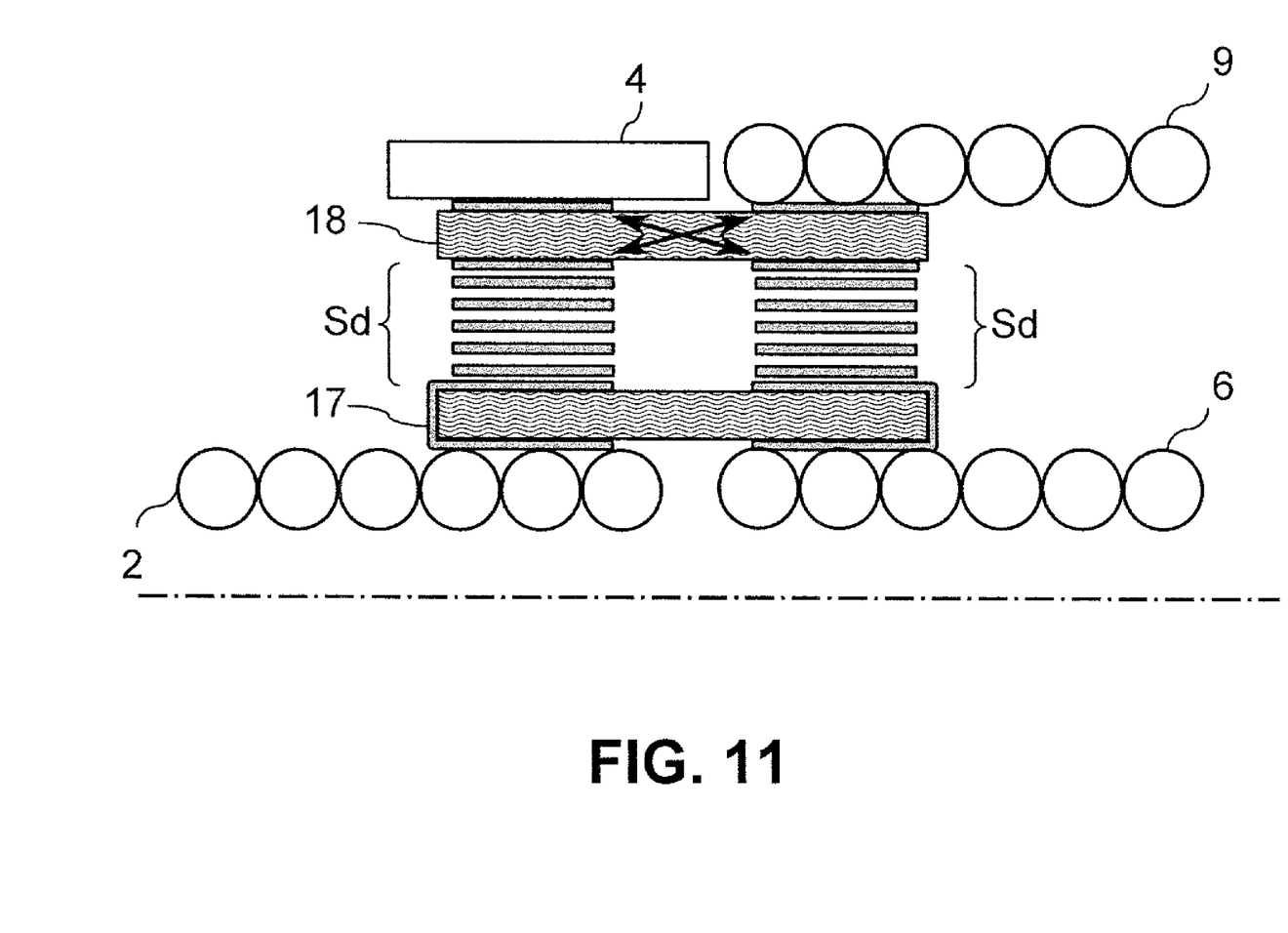
FIG. 11: A schematic representation of another exemplary stimulation electrode lead with a tubular structure with integrated lead crossover for the electrical connection.

FIG. 11 shows a further version of the stimulation electrode lead 5, in which two parallel conductive helices Sp, Sd are arranged between two ceramic tubes. The ceramic tube 18, which is connected to the second electrode 4 and the outer supply lead 9, has an integrated lead crossover, as shown in FIG. 10. The ceramic tube 17, which is connected to the electrode 2 and the inner supply lead 6, in contrast has metallizations only on the outer surface. The proximal and distal spirals Sp, Sd guarantee the electrical connection between the inner supply lead 6 and the second electrode 4 or between the outer supply lead 9 and the first electrode 2 through the lead crossover of the ceramic tube 18.

The invention is not restricted to the examples and features described above, and a variety of modifications are possible which lie within the ability of one skilled in the art. The invention therefore extends to all versions literally or equivalently encompassed by the claims below.

What is claimed is:

1. A implantable medical electrical stimulation lead (5) including a coaxial lead structure with:
   a. an inner supply lead (6),
   b. an outer supply lead (9) situated radially outwardly from, and being electrically insulated from, the inner supply lead (6), and
   c. first and second electrodes (2, 4) provided at or near to a distal end of the lead structure, wherein one of the first and second electrodes (2, 4) is movable with respect to the other about the axis of the lead structure,
   wherein:
   (1) the first electrode (2) is situated at a distal tip of the lead structure,
   (2) the second electrode (4) is situated proximally from the first electrode (2),
   (3) the inner supply lead (6) is electrically connected to the second electrode (4) via a second radially-extending connection,
   (4) the outer supply lead (9) is electrically connected to the first electrode (2) via a first radially-extending connection,
   (5) the first and second radially-extending connections both extend across regions having the same radial spacing from the axis of the lead structure.

2. The electrical stimulation lead (5) of claim 1 wherein at least a portion of the first electrode (2) is situated radially inwardly from the second electrode (4).

3. The electrical stimulation lead (5) of claim 1 wherein:
 a. the electrical connection between the inner supply lead (6) and the second electrode (4), and
 b. the electrical connection between the outer supply lead (9) and the first electrode (2), cross each other in the radial direction about at least a portion of the circumference of the lead structure.

4. The electrical stimulation lead (5) of claim 1 wherein the electrical connection between the outer supply lead (9) and the first electrode (2) extends between the inner supply lead (6) and the second electrode (4).

5. The electrical stimulation lead (5) of claim 1 wherein:
 a. the inner supply lead (6) is rotatable relative to the outer supply lead (9), and
 b. the first electrode (2) displaces relative to the second electrode (4) during rotation of the inner supply lead (6) relative to the outer supply lead (9).

6. The electrical stimulation lead (5) of claim 1 wherein the inner supply lead (6) and outer supply lead (9) are connected by threading, whereby the inner supply lead (6) and outer supply lead (9) are rotationally and translatably connected.

7. The electrical stimulation lead (5) of claim 1 further including flexible electrical connecting leads (14, 15) extending in electrical communication between:
 a. between the inner supply lead (6) and the second electrode (4), and
 b. between the outer supply lead (9) and the first electrode (2).

8. The electrical stimulation lead (5) of claim 7 wherein the electrical connecting leads (14, 15) are stretchable.

9. The electrical stimulation lead (5) of claim 7 wherein the electrical connecting leads (14, 15) are helically wound.

10. The electrical stimulation lead (5) of claim 7 wherein the electrical connecting leads (14, 15) are helically wound about the inner supply lead (6).

11. The electrical stimulation lead (5) of claim 1 further including a spiral spring (16) with:
 a. an inner part (161) electrically connecting the inner supply lead (6) to the second electrode (4),
 b. an outer part (162) electrically connecting the outer supply lead (9) to the first electrode (2).

12. The electrical stimulation lead (5) of claim 1 further including a spiral spring (16) having a wound nonconductive substrate (S) on which a metallization (M) is located on opposing inner and outer sides of the substrate (S), wherein
 a. the metallization (M) on one side of the substrate (S) electrically connects the inner supply lead (6) to the second electrode (4), and
 b. the metallization (M) on the other side of the substrate (S) electrically connects the outer supply lead (9) to the first electrode (2).

13. The electrical stimulation lead (5) of claim 12 further including one or more rigid adapters (17), each:
 a. being situated against the spiral spring (16), the first electrode (2), and the inner supply lead (6), with the adapter (17) electrically connecting the outer supply lead (9) to the first electrode (2) while electrically isolating the first electrode (2) and the inner supply lead (6); or
 b. being situated against the spiral spring (16), the second electrode (4), and the outer supply lead (9), with the adapter (17) electrically connecting the inner supply lead (6) to the second electrode (4) while electrically isolating the second electrode (4) and the outer supply lead (9).

14. The electrical stimulation lead (5) of claim 1 further including a tubular structure (18) with an integrated lead crossover electrically connecting:
 a. the inner supply lead (6) to the second electrode (4), and
 b. the outer supply lead (9) to the first electrode (2).

15. The electrical stimulation lead (5) of claim 14 wherein the tubular structure (18) is coupled with:
 a. a distal conductive helix (Sd) electrically connecting the outer supply lead (9) to the first electrode (2), and
 b. a proximal conductive helix (Sp) electrically connecting the inner supply lead (6) to the second electrode (4).

16. The electrical stimulation lead (5) of claim 1 further including:
 a. a transfer element (13) extending between the inner supply lead (6) and the first electrode (2), wherein the inner supply lead (6), the transfer element (13), and the first electrode (2) are extensible with respect to the outer supply lead (9), and
 b. a spring connected to the transfer element (13), the spring urging the transfer element (13) and the first electrode (2) into a specific position with respect to the outer supply lead (9).

17. The electrical stimulation lead (5) of claim 16 wherein the transfer element (13) and the first electrode (2) are extended with respect to the outer supply lead (9) during rotation of the inner supply lead (6).

18. The electrical stimulation lead (5) of claim 1 in connection with one of:
 a. a pacemaker (3),
 b. a defibrillator, or
 c. a neurostimulator.

19. A implantable medical electrical stimulation lead (5) having a length including:
 a. an outer supply lead (9),
 b. an inner supply lead (6) being:
  (1) electrically insulated from the outer supply lead (9), and
  (2) situated at a lesser radial distance from the lengthwise axis of the lead (5) than the outer supply lead (9),
 c. a first electrode (2) being:
  (1) exposed along an outer circumference of the lead (5),
  (2) situated distally from the inner supply lead (6) along the length of the lead (5), and
  (3) in electrical communication with the outer supply lead (9),
 d. a second electrode (4) being:
  (1) exposed along the outer circumference of the lead (5),
  (2) situated proximally from the first electrode (2) along the length of the lead (5),
  (3) situated at a greater radial distance from the lengthwise axis of the lead (5) than the first electrode (2), and
  (4) in electrical communication with the inner supply lead (6),
 wherein the first electrode (2) and second electrode (4) are respaceable along the lengthwise axis of the lead (5).

20. The electrical stimulation lead (5) of claim 19 wherein the first electrode (2) is situated distally from the outer supply lead (9) along the length of the lead (5).

21. The electrical stimulation lead (5) of claim 19 wherein:
 a. an electrical connection extends radially inwardly from the outer supply lead (9) to the first electrode (2), and
 b. an electrical connection extends radially outwardly from the inner supply lead (6) to the second electrode (4).

22. A implantable medical electrical stimulation lead (5) having a length including:
  a. an outer supply lead (9),
  b. an inner supply lead (6) situated closer to the lengthwise axis of the lead (5) than the outer supply lead (9),
  c. a first electrode (2):
    (1) electrically connected to the outer supply lead (9) and electrically insulated from the inner supply lead (6), and
    (2) being distal from the outer supply lead (9) along the length of the lead (5),
  d. a second electrode (4):
    (1) electrically connected to the inner supply lead (6) and electrically insulated from the outer supply lead (9), and
    (2) being proximal to the first electrode (2) along the length of the lead (5), wherein:
  i. the electrical connection between the first electrode (2) and the outer supply lead (9) extends radially inwardly from the outer supply lead (9) to the first electrode (2), and
  ii. the electrical connection between the second electrode (4) and the inner supply lead (6) extends radially outwardly from the inner supply lead (6) to the second electrode (4), and
  iii. the spacing between the first electrode (2) and the second electrode (4) may be varied while maintaining the electrical connection.

23. The electrical stimulation lead (5) of claim 22 wherein:
  a. the second electrode (4) is distal from the outer supply lead (9) along the length of the lead (5), and
  b. the first electrode (2) is distal from the inner supply lead (6) along the length of the lead (5).

* * * * *